United States Patent
Werner et al.

(10) Patent No.: US 8,244,226 B2
(45) Date of Patent: Aug. 14, 2012

(54) SYSTEMS AND METHODS FOR PRESENTING CHARACTERISTICS ASSOCIATED WITH A PHYSICAL ACTIVITY ROUTE

(75) Inventors: Jon Werner, Austin, TX (US); Scot Doyle, Austin, TX (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 13/081,049

(22) Filed: Apr. 6, 2011

(65) Prior Publication Data

US 2011/0191018 A1 Aug. 4, 2011

Related U.S. Application Data

(60) Division of application No. 11/932,154, filed on Oct. 31, 2007, now Pat. No. 7,941,160, which is a continuation of application No. 11/857,862, filed on Sep. 19, 2007, now Pat. No. 7,805,149, which is a continuation of application No. 10/759,289, filed on Jan. 16, 2004, now Pat. No. 7,292,867.

(60) Provisional application No. 60/440,519, filed on Jan. 16, 2003.

(51) Int. Cl.
*H04M 3/42* (2006.01)
*H04Q 7/22* (2006.01)
*H04Q 7/38* (2006.01)

(52) U.S. Cl. .................. 455/414.1; 455/456.3; 701/216; 342/357.15

(58) Field of Classification Search ................ 455/414.1, 455/422.1, 436, 440, 456.1, 456.2, 456.3; 701/207, 213–216; 342/357.01–357.09, 342/357.1–357.17
See application file for complete search history.

(56) References Cited

U.S. PATENT DOCUMENTS

| | | |
|---|---|---|
| 5,043,736 A | 8/1991 | Darnell et al. |
| 5,334,974 A | 8/1994 | Simms et al. |
| 5,400,254 A | 3/1995 | Fujita |
| 5,470,233 A | 11/1995 | Fruchterman et al. |
| 5,598,849 A | 2/1997 | Browne |
| 5,627,548 A | 5/1997 | Woo et al. |
| 5,702,323 A | 12/1997 | Poulton |
| 5,742,509 A | 4/1998 | Goldberg et al. |
| 5,751,245 A | 5/1998 | Janky et al. |
| 5,758,313 A | 5/1998 | Shah et al. |
| 5,767,795 A | 6/1998 | Schaphorst |
| 5,802,492 A | 9/1998 | DeLorme et al. |
| 5,825,327 A | 10/1998 | Krasner |
| 5,857,066 A | 1/1999 | Wyche et al. |
| 5,908,464 A | 6/1999 | Kishigami et al. |
| 5,910,799 A | 6/1999 | Carpenter et al. |
| 5,919,239 A | 7/1999 | Fraker et al. |

(Continued)

OTHER PUBLICATIONS

Garmin International, Inc., "GPSII, Garmin Owner's Manual 7 Reference," Garmin Corp., Kansas, USA, Aug. 1996, 108 pgs.

(Continued)

*Primary Examiner* — Nhan Le
(74) *Attorney, Agent, or Firm* — Sterne, Kessler, Goldstein & Fox P.L.L.C.

(57) ABSTRACT

In at least one embodiment, a method for execution by a server computer system includes receiving a description of a fitness activity of interest to a user, in response to receiving the description, identifying a route corresponding to the activity of interest, and initiating the presentation of a route rating associated with the route that is based upon at least one individual rating associated with the route.

42 Claims, 13 Drawing Sheets

U.S. PATENT DOCUMENTS

| | | | |
|---|---|---|---|
| 5,938,721 A | 8/1999 | Dussell et al. | |
| 5,948,040 A | 9/1999 | DeLorme et al. | |
| 5,976,083 A | 11/1999 | Richardson et al. | |
| 6,002,982 A | 12/1999 | Fry | |
| 6,009,138 A | 12/1999 | Slusky | |
| 6,013,007 A | 1/2000 | Root et al. | |
| 6,032,108 A | 2/2000 | Seiple et al. | |
| 6,198,431 B1 | 3/2001 | Gibson | |
| 6,208,935 B1 * | 3/2001 | Yamada et al. | 701/209 |
| 6,212,469 B1 | 4/2001 | Knepper | |
| 6,246,362 B1 | 6/2001 | Tsubata et al. | |
| 6,251,048 B1 | 6/2001 | Kaufman | |
| 6,450,922 B1 * | 9/2002 | Henderson et al. | 482/8 |
| 6,463,385 B1 | 10/2002 | Fry | |
| 6,513,532 B2 | 2/2003 | Mault et al. | |
| 6,585,622 B1 | 7/2003 | Shum et al. | |
| 6,601,016 B1 | 7/2003 | Brown et al. | |
| 6,605,038 B1 | 8/2003 | Teller et al. | |
| 6,716,139 B1 | 4/2004 | Hosseinzadeh et al. | |
| 6,736,759 B1 | 5/2004 | Stubbs et al. | |
| 6,746,370 B1 | 6/2004 | Fleming et al. | |
| 6,790,178 B1 | 9/2004 | Mault et al. | |
| 6,798,378 B1 | 9/2004 | Walters | |
| 6,823,036 B1 | 11/2004 | Chen | |
| 6,837,827 B1 | 1/2005 | Lee et al. | |
| 6,845,321 B1 | 1/2005 | Kerns | |
| 6,853,955 B1 | 2/2005 | Burrell et al. | |
| 6,872,077 B2 | 3/2005 | Yeager | |
| 6,918,858 B2 | 7/2005 | Watterson et al. | |
| 6,921,351 B1 | 7/2005 | Hickman et al. | |
| 7,062,225 B2 | 6/2006 | White et al. | |
| 7,070,539 B2 | 7/2006 | Brown et al. | |
| 7,216,034 B2 | 5/2007 | Vitikainen et al. | |
| 7,217,224 B2 | 5/2007 | Thomas | |
| 7,254,516 B2 | 8/2007 | Case et al. | |
| 7,292,867 B2 | 11/2007 | Werner et al. | |
| 7,480,512 B2 | 1/2009 | Graham et al. | |
| 7,518,054 B2 | 4/2009 | McKinney et al. | |
| 7,670,263 B2 | 3/2010 | Ellis et al. | |
| 7,706,815 B2 | 4/2010 | Graham et al. | |
| 7,805,149 B2 | 9/2010 | Werner et al. | |
| 7,805,150 B2 | 9/2010 | Graham et al. | |
| 7,941,160 B2 | 5/2011 | Werner et al. | |
| 7,953,549 B2 | 5/2011 | Graham et al. | |
| 7,957,752 B2 | 6/2011 | Werner et al. | |
| 2001/0027375 A1 | 10/2001 | Machida et al. | |
| 2002/0049535 A1 | 4/2002 | Rigo et al. | |
| 2002/0094776 A1 | 7/2002 | Pulver | |
| 2002/0102988 A1 | 8/2002 | Myllymaki | |
| 2002/0107433 A1 | 8/2002 | Mault | |
| 2003/0100315 A1 | 5/2003 | Rankin | |
| 2003/0171189 A1 | 9/2003 | Kaufman et al. | |
| 2003/0191578 A1 | 10/2003 | Paulauskas et al. | |
| 2003/0208409 A1 | 11/2003 | Mault | |
| 2003/0224337 A1 | 12/2003 | Shum et al. | |
| 2003/0229446 A1 | 12/2003 | Boscamp et al. | |
| 2004/0046692 A1 | 3/2004 | Robson et al. | |
| 2004/0102931 A1 | 5/2004 | Ellis et al. | |
| 2004/0199056 A1 | 10/2004 | Husemann et al. | |
| 2004/0203789 A1 | 10/2004 | Hammond et al. | |
| 2004/0203873 A1 | 10/2004 | Gray | |
| 2004/0249846 A1 | 12/2004 | Randall et al. | |
| 2005/0096933 A1 | 5/2005 | Collins et al. | |
| 2005/0121504 A1 | 6/2005 | Sanders et al. | |
| 2005/0172311 A1 | 8/2005 | Hjelt et al. | |
| 2005/0195094 A1 | 9/2005 | White | |
| 2005/0197063 A1 | 9/2005 | White | |
| 2005/0266961 A1 | 12/2005 | Shum et al. | |
| 2005/0287499 A1 | 12/2005 | Yeager | |
| 2006/0082472 A1 | 4/2006 | Adachi et al. | |
| 2006/0156356 A1 | 7/2006 | Sato et al. | |
| 2006/0189360 A1 | 8/2006 | White | |
| 2006/0240865 A1 | 10/2006 | White | |
| 2007/0287596 A1 | 12/2007 | Case et al. | |
| 2010/0042427 A1 | 2/2010 | Graham et al. | |
| 2011/0082641 A1 | 4/2011 | Werner et al. | |

OTHER PUBLICATIONS

Garmin International, Inc., "GPSIII, Garmin Owner's Manual 7 Reference," Garmin Corp., Kansas, USA, Aug. 1997, 100 pgs.

Garmin International, Inc., "NAVTALK; Cellular Phone/GPS Receiver; Owner's Manual and Reference Guide," Garmin Corporation, 1999-2000.

Garmin LTD; NAVTALK; Product information; 6 pages, 2002.

Magellan Systems Corporation, "Magellan GPS, NANDLX-10 User Guide," 1995, pp. 1-91.

Magellan Systems Corporation, "Magellen GPS Satellite Navigator Referece Guide Trailblazer XL," 1995, pp. 1-78.

Mehaffey et al., "Garmin's NavTalk Cell Phone and Road Map GPS Product Review" Revision 2, Nov. 2, 1999, 5 pgs.

Sawhney et al., "Speaking and Listening on the Run: Design for Wearable Audio Computing," Speech Interface Group, MIT Media Laboratory, Oct. 19-20, 1998.

GPSII, Garmin Owner's Manual & Reference, 108 pages, Aug. 1996, Garmin Corp., Kansas, USA.

GPSIII, Garmin Owner's Manual & Reference, 100 pages, Aug. 1997, Garmin Corp., Kansas, USA.

Garmin International, Inc., "NAVTALK; Cellular Phone/GPS Receiver; Owner's Manual and Reference Guide," 1999-2000, Garmin Corporation, 128 pages.

* cited by examiner

SYSTEMS AND METHODS FOR PRESENTING CHARACTERISTICS ASSOCIATED WITH A PHYSICAL ACTIVITY ROUTE

CROSS REFERENCE TO RELATED APPLICATIONS

The present application is a divisional of U.S. patent application Ser. No. 11/932,154, filed Oct. 31, 2007, which is a continuation of U.S. patent application Ser. No. 11/857,862, filed Sep. 19, 2007, now U.S. Pat. No. 7,805,149, which is a continuation of U.S. patent application Ser. No. 10/759,289, filed Jan. 16, 2004, now U.S. Pat. No. 7,292,867, which claims priority to U.S. Provisional Patent App. No. 60/440,519, filed Jan. 16, 2003. These applications are hereby incorporated herein by reference in their entireties.

BACKGROUND OF THE INVENTION

1. Field of the Invention

The present invention relates to systems and methods for presenting characteristic associated with a physical activity route.

2. Related Art

As Global Positioning System (GPS) technology has matured, location-aware electronics have been integrated into a number of different mobile platforms, such as automobiles, mobile telephones, two-way radios, and hand-held GPS receivers, in order to provide location-based information. U.S. Pat. No. 6,013,007 to Root et al., which is incorporated herein by reference, discloses that a UPS receiver may additionally be implemented within an athlete's portable performance monitor to enable the performance monitor to record and to present the athlete with accurate performance information, such as distance traveled and pace.

BRIEF SUMMARY OF THE INVENTION

Embodiments of the present invention relate to a method for execution by a server computer system, the method including receiving a description of a fitness activity of interest to a user, in response to receiving the description, identifying a route corresponding to the activity of interest, and initiating the presentation of a route rating associated with the route that is based upon at least one individual rating associated with the route.

Embodiments of the present invention also relate to a computer program product comprising computer-useable medium having computer program logic recorded thereon that, when executed by one or more processors of a server computer system, provides information about a route corresponding to a fitness activity of interest to a user, the computer program logic including first computer readable program code that enables a processor to receive a description of the fitness activity of interest to the user, second computer readable program code that enables a processor to, in response to receiving the description, identify a route corresponding to the activity of interest, and third computer readable program code that enables a processor to initiate the presentation of a route rating associated with the route that is based upon at least one individual rating associated with the route.

Embodiments of the present invention further relate to a method for execution by one or more processors, the method including receiving a description of a fitness activity of interest to a user, in response to receiving the description, identifying a route corresponding to the activity of interest, and displaying a characteristic associated with the route that is based upon at least one individual input associated with the route.

Embodiments of the present invention still further relate to a method for execution by a computer, the method including receiving route data that is associated with a fitness activity engaged in by a first user, presenting a GUI element that permits the first user to assign an individual rating to the route, receiving the individual rating from the first user, and transmitting the individual rating to a route database that is accessible by users other than the first user.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The novel features believed characteristic of the invention are set forth in the appended claims. However, the invention, as well as a preferred mode of use, will best be understood by reference to the following detailed description of an illustrative embodiment when read in conjunction with the accompanying drawings, wherein:

Figure 5A:
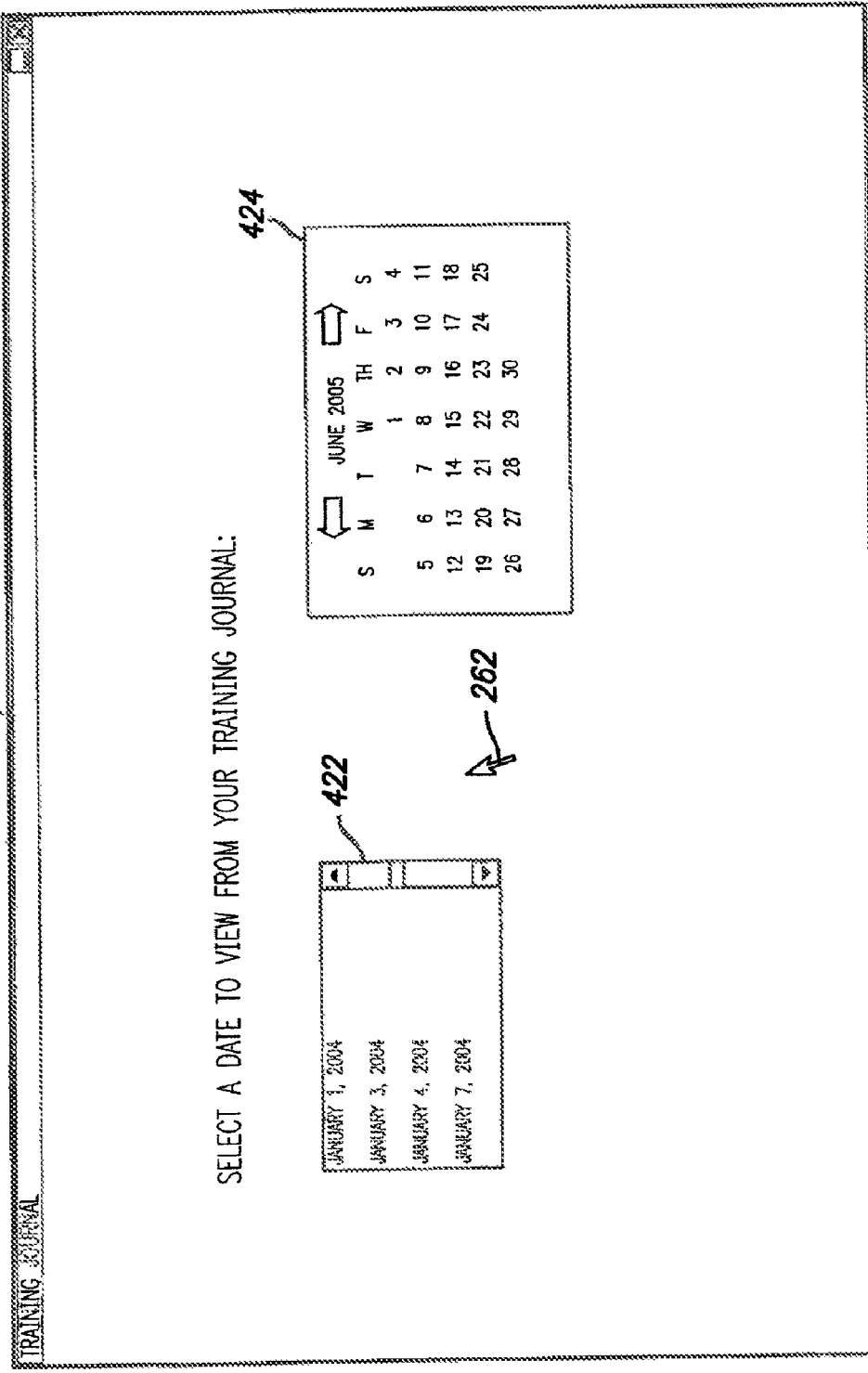
FIG. 5A illustrates an exemplary graphical user interface of a training journal through which a user may view routes traversed with a portable fitness device in accordance with the present invention.
Figure 5B:
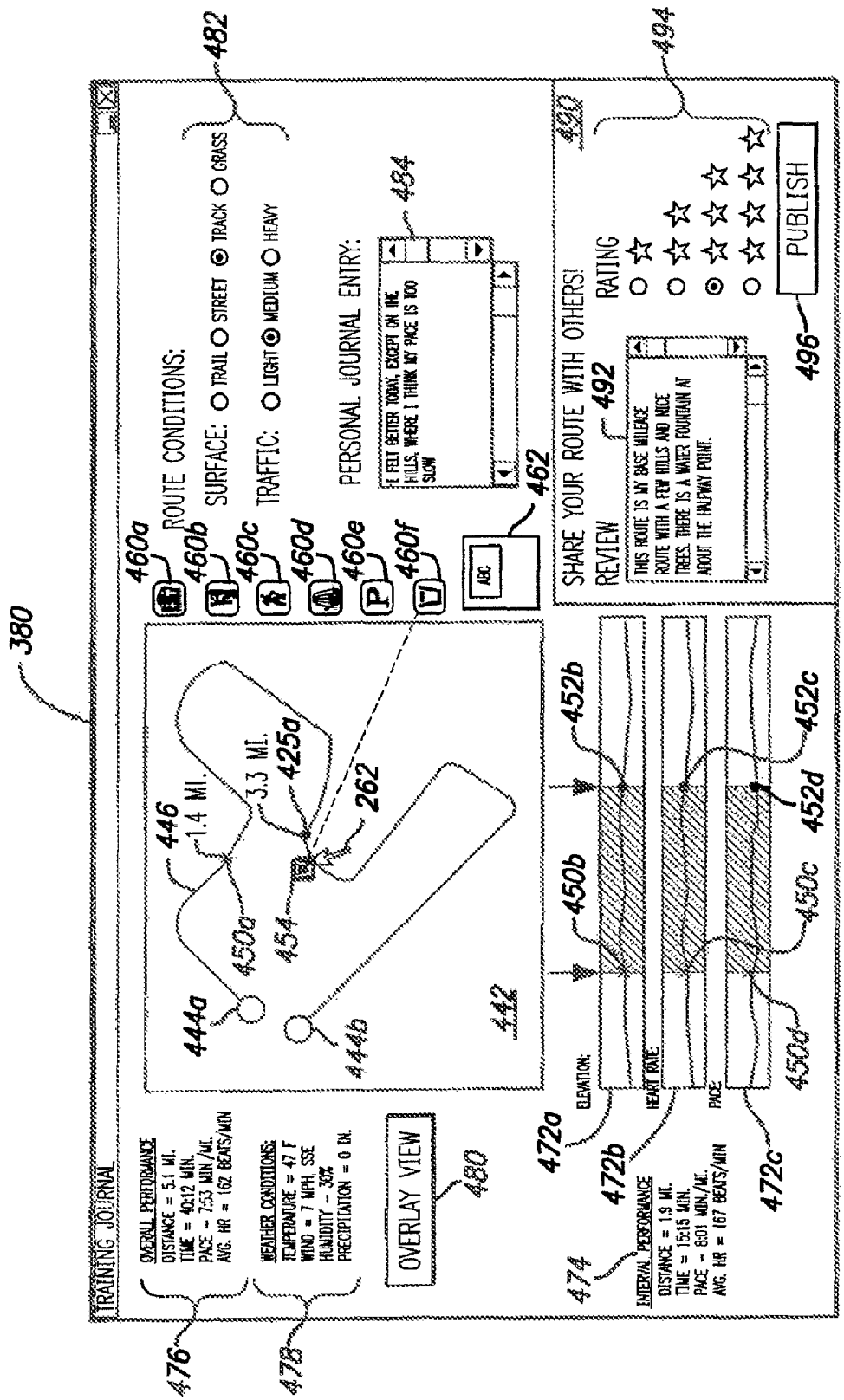
Figure 5C:
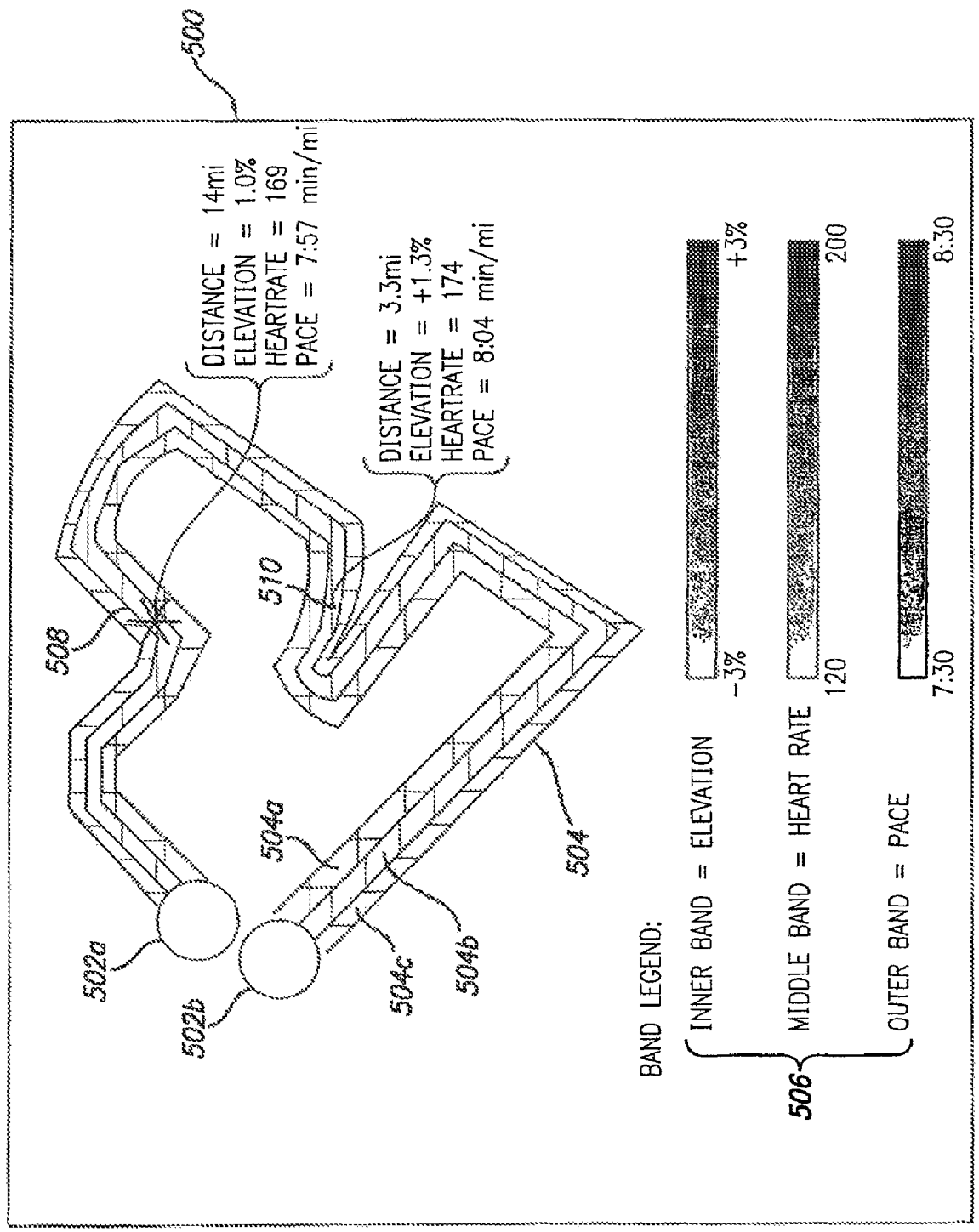

FIG. 5B depicts an exemplary graphical user interface of a training journal entry detailing a particular route traversed with a portable fitness device in accordance with the present invention; and FIG. 5C illustrates an exemplary graphical user interface of a training journal entry showing a route view in which multiple route and/or performance parameters are concurrently graphically presented in a banded format along a route path.

DETAILED DESCRIPTION OF THE INVENTION

Figure 1:
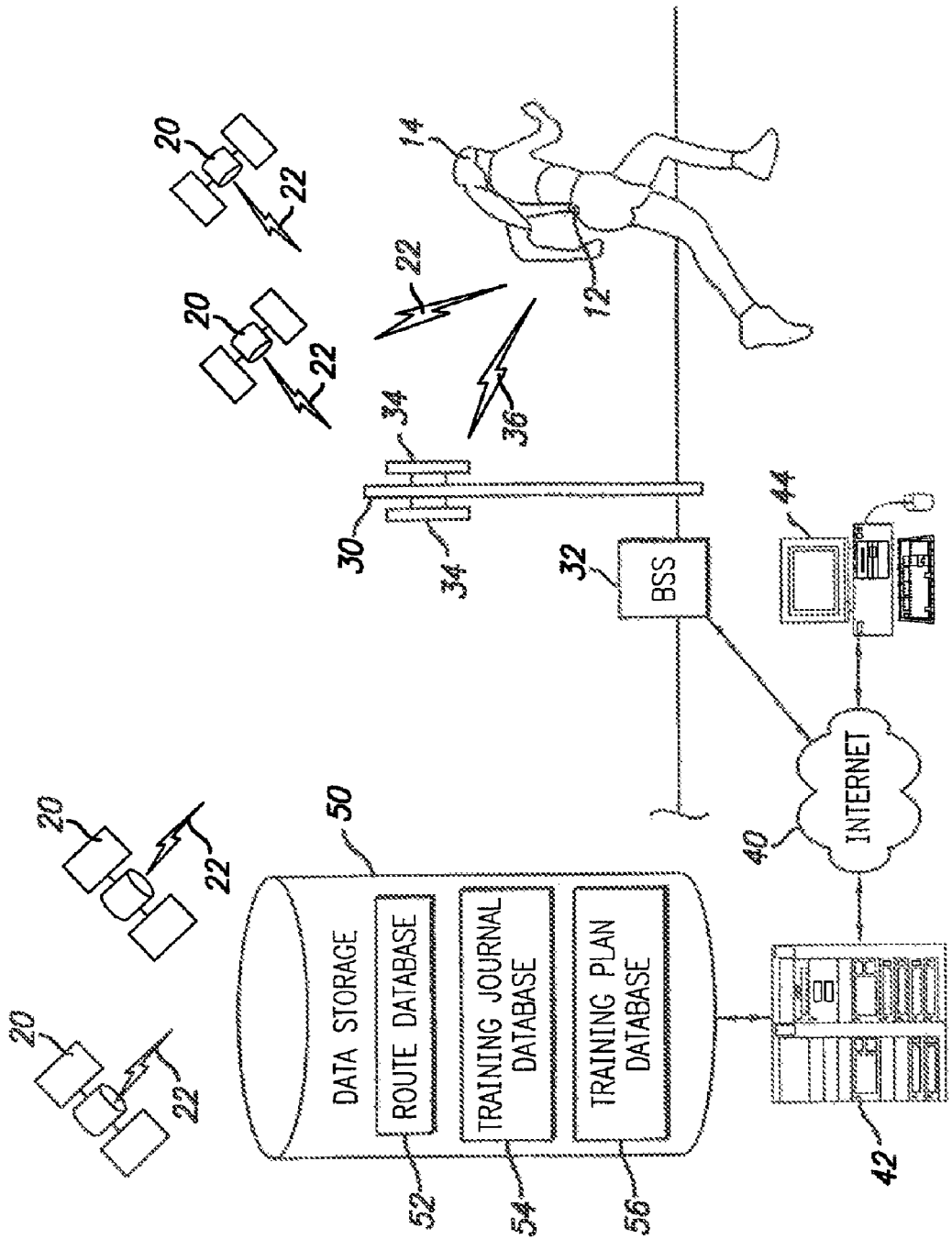
FIG. 1 is a schematic diagram of an exemplary environment in which the present invention may be practiced.

With reference now to the figures, and in particular with reference to FIG. 1, there is depicted an exemplary embodiment of an environment in which the methods, systems, and program products of the present invention may advantageously be practiced. In particular, FIG. 1 illustrates an environment 10 in which a location-aware portable fitness device 12 is utilized by an athlete 14 while engaged in a fitness activity, such as running, cycling, hiking, skiing, etc.

As shown, environment 10 includes a constellation of earth-orbiting global positioning system (GPS) satellites 20. As is known in the art, GPS satellites 20 continuously emit GPS signals 22, which enable GPS-equipped devices, such as portable fitness device 12, to continuously determine their position, velocity, and bearing as long as a sufficient number of GPS satellites 20 can be acquired.

Environment 10 further includes a wireless wide-area network (WAN) communication system including a plurality of geographically distributed cellular telephone towers 30 and base station systems (BSS) 32 (only one of each is illustrated for simplicity). Cellular telephone tower 30 includes one or more antennae 34 supporting long range two-way radio frequency communication with mobile telephones and other wireless devices, such as portable fitness device 12. The radio frequency communication between antennae 34 and portable fitness device 12 may utilize radio frequency signals 36 conforming to any known or future developed wireless protocol, for example, CDMA, GSM, EDGE, 3G, etc. The information transmitted over-the-air by BSS 32 and cellular communication tower 30 to portable fitness device 12 may be further transmitted to or received from one or more additional circuit-switched or packet-switched communication networks, including, for example, the Internet 40.

As is well known to those skilled in the art, Internet 40 is a worldwide collection of servers, routers, switches and transmission lines that employ the Internet Protocol (IP) to communicate data. For example, Internet 40 may be employed to communicate data between any of server computer system 42, client computer system 44, and portable fitness device 12. For example, as described further below, Internet 40 may be utilized to communicate to portable fitness device 12 route information from a route database 52 stored within data storage 50 associated with server computer system 42. Similarly, portable fitness device 12 may transmit route and performance information to server computer system 42 for storage in training journal database 54 via Internet 40, BSS 32, and cellular communication tower 30. In addition, a user stationed at a remote client computer system 44, for example, athlete 14 or a remote trainer, may access real-time or historical performance information regarding the training of athlete 14 via server computer system 42 and Internet 40.

Figure 2A:
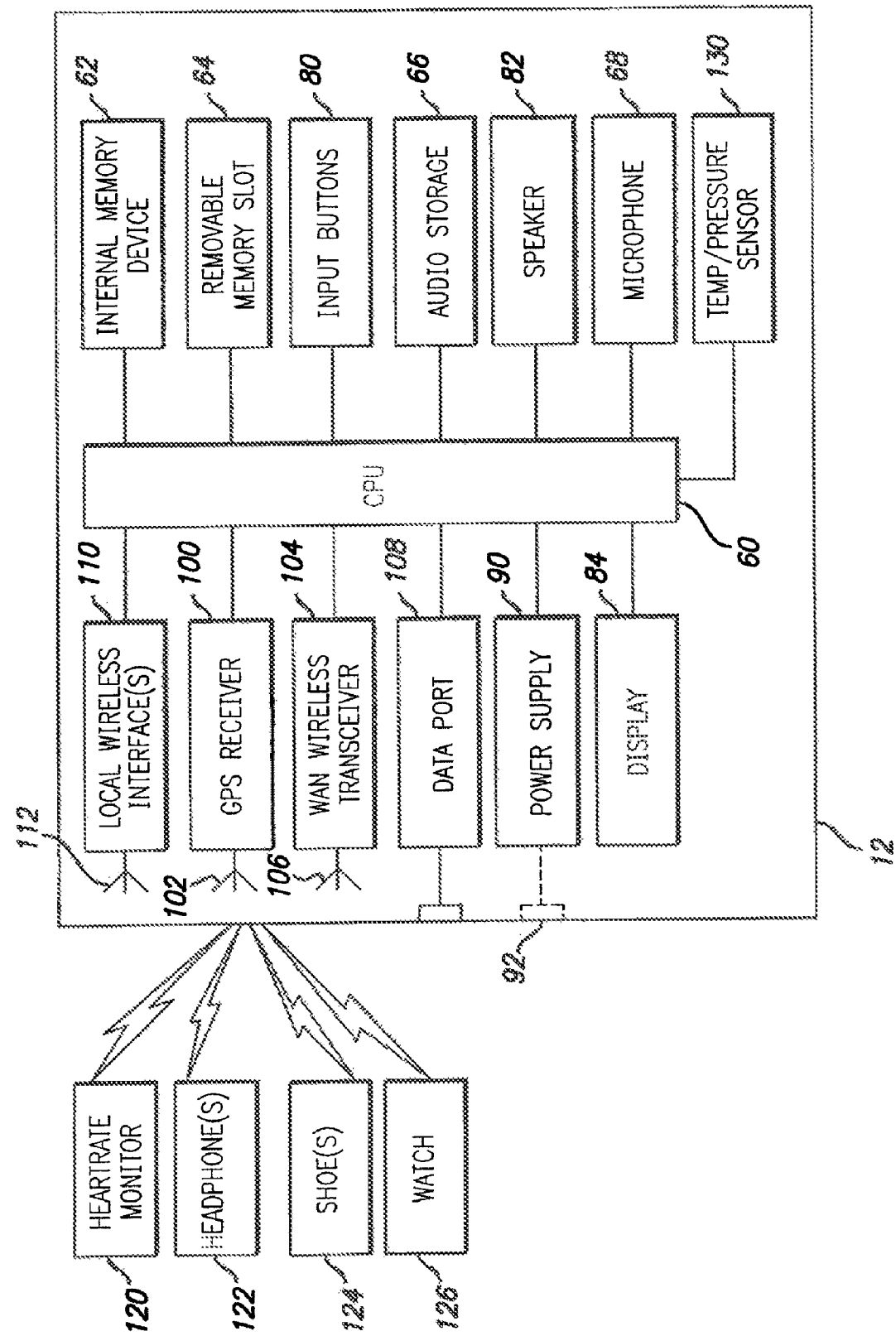
FIG. 2A is a schematic block diagram of an illustrative portable fitness device in accordance with the present invention.

Referring now to FIG. 2A, there is illustrated a high-level block diagram of an exemplary implementation of portable training device 12 in accordance with the present invention. As illustrated, portable training device 12 includes a central processing unit (CPU) 60 that controls the operation of portable fitness device 12 in accordance with client software 154 described further below with respect to FIG. 2B. As shown, CPU 60 is coupled, either directly or indirectly to a variety of different components within portable fitness device 12. For example, portable fitness device 12 includes an internal memory device 62 for storing the client software, as well as various route, performance and environmental information regarding a training activity of athlete 14. The storage provided by internal memory device 62 may be further augmented by a removable storage medium inserted within removable memory slot 64 and/or dedicated audio storage 66 for storing audio data. The audio data may include, for example, music tracks encoded in MP3 format, synthesized human speech tracks, voice annotations by athlete 14 recorded via an internal or external microphone 68, as well as other audio data.

In addition to microphone 68, portable fitness device 12 may include a number of other input/output (I/O) devices. For example, portable fitness device 12 may include one or more manually manipulable input buttons 80 that permit athlete 14 to annotate a route while athlete 14 is traversing the route and/or to enter desired settings of portable fitness device 12. Portable fitness device 12 may also include a speaker 82 and display 84 through which portable fitness device 12 may present real-time performance information (e.g., elapsed distance, elapsed time, pace, distance to go, heart rate, etc.), turn-by-turn directions, real-time remote training recommendations, and other information in either an audio or visual format.

Portable fitness device 12 is equipped with a power supply 90 that powers CPU 60 and the other components of portable fitness device 12. Power supply 90 includes a battery and may further have an associated power port 92 through which the battery may be charged from an AC power source. Alternatively, the battery within power supply 90 may be charged utilizing a wireless inductive charging device, as is known in the art.

Portable fitness device 12 further includes a GPS receiver 100 and associated GPS antenna 102 that receive GPS signals 22 from GPS satellites 20. GPS receiver 100 processes GPS signals 22 to present to CPU 60 time-stamped waypoints, which include at least a time, a latitude, and a longitude. If at least four GPS satellites 20 have been acquired, the time-stamped waypoints presented to CPU 60 by GPS receiver 100 preferably further include an elevation. As discussed further below, the time and position information supplied by GPS receiver 100 is utilized by client software 154 running on CPU 60 to build a record of a route traversed by athlete 14 and to determine performance information (e.g., elapsed distance, elapsed time, pace, distance to go, heart rate, etc.) regarding the athlete's traversal of the route.

Portable training device 12 supports two-way wireless WAN communication with cellular telephone tower 30 with WAN wireless transceiver 104 and its associated antenna 106. As known to those skilled in the art, WAN wireless transceiver 104 includes a receiver for receiving radio frequency signals 36 and a transmitter for transmitting radio frequency signals 36. As discussed in greater detail below, radio frequency signals 36 may include route information transmitted to portable fitness device 12, route and performance information transmitted from portable fitness device 12, settings for portable fitness device 12, and one or two-way voice communication (e.g., a voice conversation between athlete 14 and a remote trainer stationed at remote client computer 44). The data sent and received by WAN wireless transceiver 104 may alternatively be communicated via an optional data port 108, which may employ short range wired or wireless communication (e.g., RS-232 or infrared).

In order to support communication with other electronics within close range, portable fitness device 12 may be further equipped with one or more local wireless interface(s) 110 and associated antennae 112. For example, local wireless interface(s) may include interfaces for 802.11x, Bluetooth, 900 mHz communication or the like. Utilizing such technologies, portable fitness device 12 may communicate with or sense data from a heart rate monitor 120, headphones 122, shoes 124, and a watch 126 worn by athlete 14 during a fitness activity. In this manner, portable fitness device 12 may gather information regarding athlete 14, such as his/her heart rate and body temperature, and if the athlete's shoes 124 are equipped with an RFID tag, the shoes 124 worn during the fitness activity. Portable fitness device 12 may similarly present to the user performance, directional and training information via watch 126 and headphones 122.

Of course, in alternative embodiments, portable fitness device 12 may sense or communicate with particular devices utilizing wired or wireless interfaces. For example, microphone 68 may alternatively be incorporated within wireless headphones 122, and heart rate monitor 120 may alternatively be coupled to CPU 60 via a wired interface. Thus, those skilled in the art will appreciate from the block diagram provided in FIG. 2A, that any number of internal or external devices and sensors, such as temperature and barometric pressure sensor 130, may be coupled to CPU 60 via either wired or wireless interfaces. In this manner, client software running on CPU 60 may associate with the time and position information provided by GPS receiver 100 various data of interest regarding athlete 14, his/her environment and the route being traversed. The data may be stored locally by portable fitness device 12, for example, within internal memory device 62, or transmitted over-the-air by WAN wireless transceiver 104, possibly in real time.

Figure 2B:
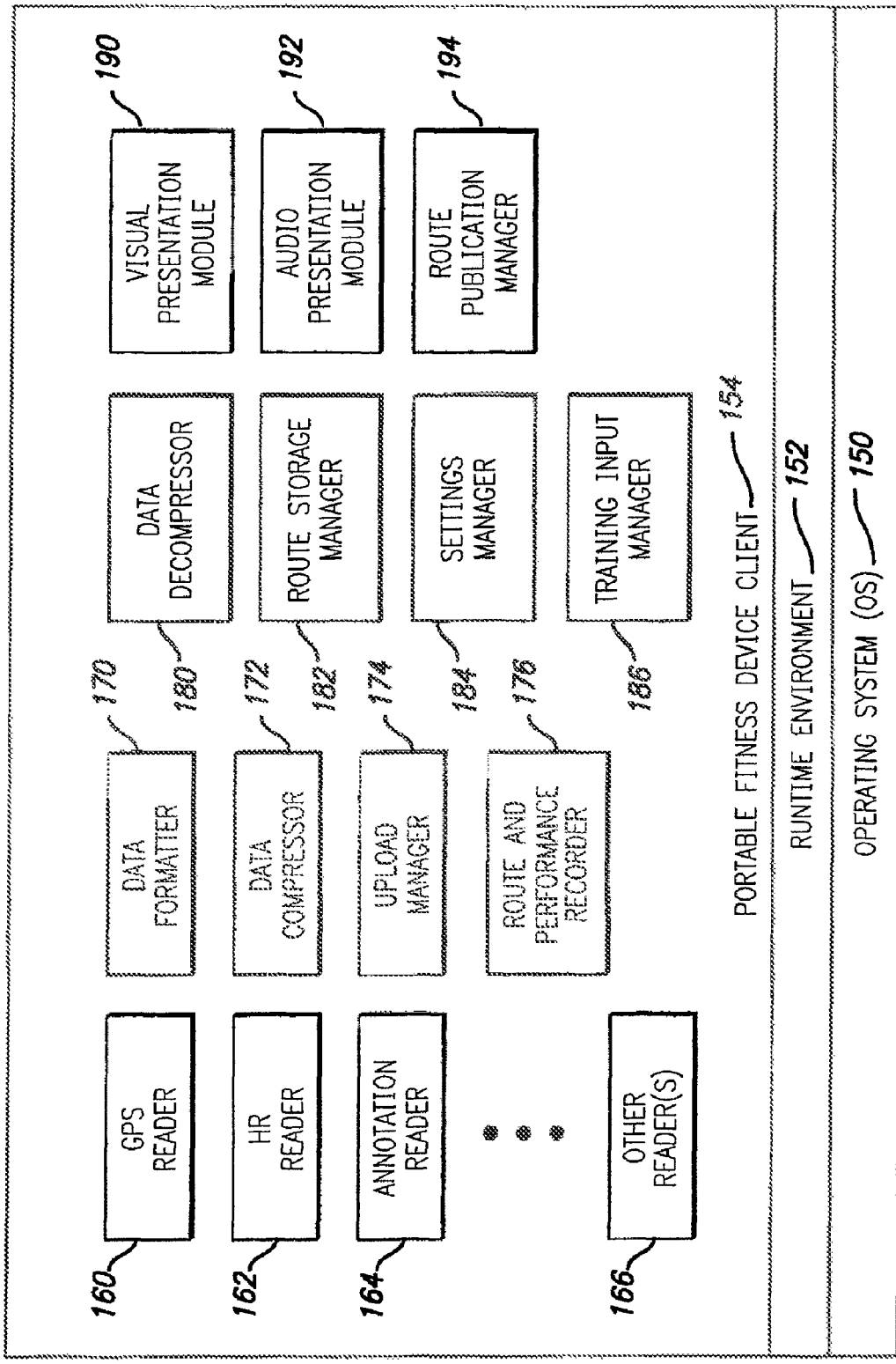
FIG. 2B is a layer diagram of an exemplary software configuration of a portable fitness device in accordance with the present invention.

With reference now to FIG. 2B, there is illustrated a layer diagram of an exemplary software configuration of portable fitness device 12 in accordance with one embodiment of the present invention. As illustrated, the software configuration of portable fitness device 12 includes at a lowest level an operating system (OS) 150 that provides a collection of services, such as thread scheduling, memory management, interrupts, etc., that may be accessed by higher-level software. Running on top of operating system 150 is a runtime environment 152, such as one of the JAVA or BREW runtime environments. Finally, the software configuration of portable fitness device 12 includes a portable fitness device client 154 running on top of runtime environment 152. Portable fitness device client 154 may be downloaded to portable fitness device 12 over-the-air, for example, via the wireless WAN and WAN wireless transceiver 104.

As illustrated, portable fitness device client 154 comprises a number of individual modules, each performing a function of portable fitness device 12. Those skilled in the art will appreciate that the illustrated modules are illustrative rather than exhaustive, and that portable fitness device client 154 may include additional or alternative modules to support or extend the functionality of portable fitness device 12.

As shown in FIG. 2B, the modules within portable fitness device client 154 preferably include a number of reader modules 160-166. GPS reader 160 receives from GPS receiver 100 time-stamped waypoints including at least time, latitude and longitude information, and, depending upon implementation and the number of GPS satellites 20 from which GPS signals 22 were received, elevation and error information. Utilizing the time-stamped waypoints received from GPS receiver 100, GPS reader 160 calculates performance and route information for athlete 14. For example, GPS reader 160 may determines the start time at which a route was begun, an elapsed time, an elapsed distance, distance remaining in the route, elevation change, average elevation, current pace, average pace, bearing, etc.

The remainder of readers 160-166, for example, heart rate reader 162 and annotation reader 164, similarly obtain input data and associate the input data with a corresponding time-stamped waypoint obtained by GPS reader 160. Readers 162-166 may also perform additional calculations to determine instantaneous, differential or cumulative quantitative characterizations of the route, the performance of athlete 14 or of his/her environment. Thus, for example, heart rate reader 162 may obtain an instantaneous heart rate reading from heart rate monitor 120, associate that heart rate reading with the time-stamped waypoint obtained by GPS reader 160, and calculate an average heart rate. Similarly, annotation reader 164 may store a route annotation entered by athlete 14 via input buttons 80 or microphone 18 with a time-stamped waypoint obtained by GPS reader 160.

The data gathered and calculated by readers 160-166 are then parsed and formatted by formatter 170 into a predetermined data format that associates the performance and route data with a timestamp and geographical location. The particular data format employed by data formatter 170 is implementation-dependent, but is preferably compact to conserve the capacity of internal memory device 62 and the bandwidth of the communication link between portable training device 12 and the wireless WAN. Storage capacity and wireless communication bandwidth may further be conserved by applying a data compressor 172 to the formatted data produced by data formatter 170.

After data obtained and calculated by readers 160-166 have been formatted by data formatter 170 and optionally compressed by data compressor 172, the data are either stored within internal memory device 62 (or audio storage 66 or a removal memory loaded in removable memory slot 64) or are transmitted over-the-air via WAN wireless transceiver 104. Upload manager 174 and route and performance recorder 176 determine whether or not to upload and/or store data locally based upon one or more criteria, for example, whether WAN wireless transceiver 104 can acquire a connection to the wireless WAN, the available storage within internal memory device 62, an indication of whether or not a remote user is tracking the training of athlete 14 in real-time, and/or other criteria. If, based upon these and/or other criteria, upload manager 174 decides to upload the formatted and compressed data, upload manager 174 outputs the data via WAN wireless transceiver 104 and antenna 106 to client computer system 44 and/or server computer system 42 utilizing radio frequency signals 36. Data transmitted to client computer system 44 is typically graphically presented within a display device, and data transmitted to server computer system 42 is typically stored within training journal database 54.

As noted above, portable training device 12 may alternatively receive data over-the-air from the wireless WAN. In a preferred embodiment, the data received over-the-air from the wireless WAN may include route information transmitted by server computer system 42 from route database 52, settings of portable fitness device 12 transmitted by server computer system 42 or client computer system 44, and training recommendations transmitted from server computer system 42 or client computer system 44. Route information, which may be identified as such, for example, by an XML header, is received, processed and stored by route storage manager 182. The route information may be, for example, turn-by-turn directions keyed to particular geographical areas defined by a latitude and longitude range duple. By storing route information in this format, when GPS reader 160 obtains a time-stamped waypoint falling within a particular geographic area defined by a latitude and longitude range duple, audio presentation module 192 can present an audible instruction to athlete 14 via speaker 82 and/or headphones 122 to direct athlete 14 how to traverse a desired route.

Settings data, which may be identified as such, for example, by an XML header, is initially received, processed, and output by data decompressor 180 is then subsequently processed by settings manager 184. For example, settings manager 184 may utilize settings data to update storage locations within internal memory device 62 governing particular aspects of the operation of portable training device 12. In addition, based upon the received settings, settings manager 184 may notify upload manager 174 or route and performance recorder 176 to initiate upload or storage of route and performance information.

Training recommendations received, processed and output by data decompressor 180 are subsequently processed by training input manager 186. These training recommendations preferably take the form of either voice data communicated by a human trainer utilizing, for example, a voice-over-IP (VoIP) connection to portable training device 12, or a predetermined data command representing an audio message. In the former case, training input manager 186 exports the audio data directly to audio presentation module 192, which, in turn, directly presents the audio data to athlete 14 via headphones 122 and/or speaker 82. If, however, the training recommendation takes the form of a data command representing an audio message, training input manager 186 locates an audio track within audio storage 66 or internal memory device 62 corresponding to the data command and presents the audio track to audio presentation module 192 for subsequent presentation to athlete 14. In this manner, a remote trainer, who may be stationed at client computer system 44, may provide training recommendations directly to athlete 14 in substantially real-time. And, if portable training device 12 is equipped with a microphone 68, athlete 14 may similarly communicate audibly with the remote trainer (e.g., via VoIP) through the execution of annotation reader 164 data formatter 170, data compressor 172 and upload manager 174.

Audio presentation module 192 is also preferably equipped to present, in audio format, turn-by-turn directions correcting the course of an athlete 14 to return to a route if a turn is missed, as well as turn-by-turn directions providing the most direct return path to the starting point. Such turn-by-turn directions are preferably computed by server computer system 42 based upon real time location information received over-the-air from portable fitness device 12 and then transmitted to portable fitness device 12, again utilizing over-the-air communication via the wireless WAN. Audio presentation module 192 may also be utilized to decode and present audio entertainment tracks, such as the MP3 files stored within audio storage 66.

As further depicted in FIG. 2B, portable fitness device client 154 includes a visual presentation module 190 that manages the presentation of route, performance and environmental information to athlete 14 via optional display 84 and/or the display of watch 126. It should be noted, however, that it is presently preferred to present data of all types to athlete 14 during the course of a fitness activity in audio format so that the concentration and attention of athlete 14 is not diverted from training efforts.

Finally, route publication manager 194 of portable fitness device client 154 supports the sharing of routes between multiple portable fitness devices 12, for example, utilizing the local wireless interface 110, WAN wireless transceiver 104, or data port 108. In this manner, an athlete 14 can directly share selected routes (e.g., as identified utilizing input buttons 80) to other athletes having compatible portable fitness devices 12.

Figure 3:
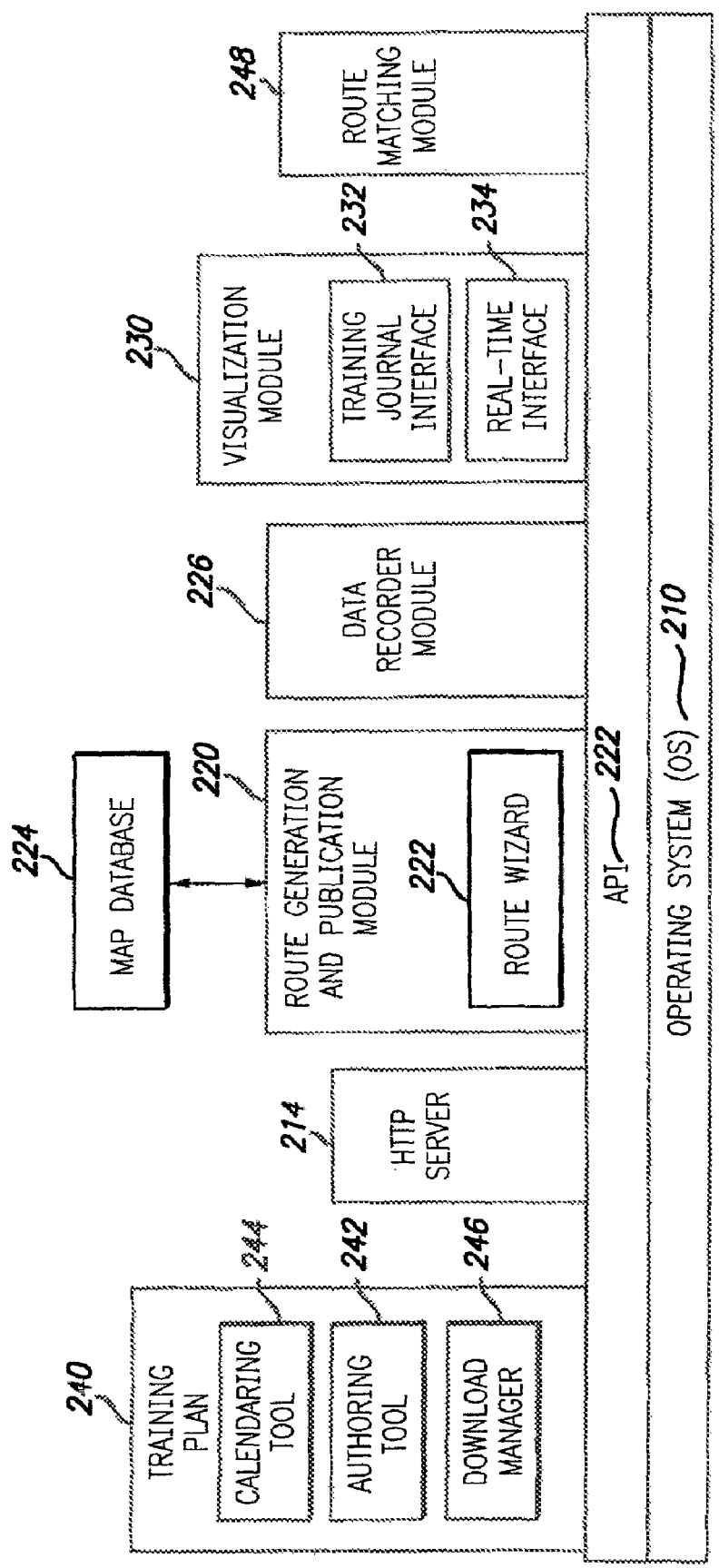
FIG. 3 is a layer diagram of an illustrative software configuration of a server computer system providing an automated web-based route generation, route journaling and route visualization service in accordance with the present invention.

Referring now to FIG. 3, there is depicted a layer diagram of an exemplary software configuration of server computer system 42 of FIG. 1 that, in accordance with the present invention, provides an automated web-based route generation, route journaling and route visualization service. The service may be restricted to users that have been issued login IDs and passwords, and may further be offered in exchange for a subscription fee.

As shown, at the lowest layer the software configuration of server computer system 42 includes an operating system (OS) 210, which is preferably one of the commercially available operating systems, such as Windows, UNIX, LINUX, AIX, etc. OS 210 has an associated application programming interface (API) 212 though which middleware and application programs may access the services of OS 210.

Running on top of OS 210 is a hypertext transport protocol (HTTP) server 214, which, as is well known in the art, communicates data over Internet 40 utilizing HTTP. In particular, HTTP server 214 supports data communication with portable fitness device 12 and one or more remote client computers 44 utilizing HTTP. Communication with server computer system 42 may alternatively or additionally be conducted utilizing a sockets layer interface or other lower layer protocol running over IP.

In addition to HTTP server 214, the application software of server computer system 42 includes a number of different modules supporting the client-side functionality provided by portable fitness device client 154. In the depicted embodiment, these modules include a route generation and publication module 220, a data recorder module 226, and a visualization module 230. Those skilled in the art will again appreciate that alternative or additional modules may be implemented within server computer system 42 in order to provide or extend the described or additional functionality.

Route generation and publication module 220 generates routes to be traversed by athletes 14 during fitness activities, stores the routes within route database 52 (FIG. 1) for subsequent access, and downloads the routes to portable fitness devices 12. In a preferred embodiment, route generation and publication module 220 includes a route wizard 222, which, as described below with respect to FIG. 4A-4F, guides a user through a step-by-step process for generating routes having desired parameters and attributes. As shown in FIG. 3, route generation and publication module 220 preferably accesses a local or remote map database 224 that stores street and/or trail information in association with at least latitude and longitude information, and preferably elevation information. Thus, given at least one terminal point (e.g., a starting point), route generation and publication module 220 is able to construct one or more routes having a desired length, elevation profile, and other parameters and attributes. Routes generated by route generation and publication module 220 are stored for subsequent access within route database 52.

Once a particular route is scheduled by an athlete 14 as discussed further below, route generation and publication module 220 transforms the route into a sequence of turn-by-turn instructions and publishes the route to a portable fitness device 12 via HTTP server 214 and the wireless WAN. Because route generation and publication module 220 can obtain elevation information along a desired route directly from map database 224, route generation and publication module 220 is also able to advantageously supply, in conjunction with a route, elevation information for the route. In this manner, the elevation information supplied by route generation and publication module 220 can assist or replace the elevation information provided by GPS receiver 100. Thus, if less than four GPS satellites 20 are acquired, or if GPS receiver 100 is not designed to process elevation information, portable fitness device 12 can still determine elevation-dependent route and performance data regarding a route traversed by athlete 14.

Data recorder module 226 receives route and performance information from portable training device 12 via the wireless WAN and/or local wireless interface 110 and/or data port 108 and utilizes such data to build a virtual training journal for athlete 14 within training journal database 54. As noted previously, depending upon the operation of the upload manager 174 and route and performance recorder 176 within portable fitness device client 154, data recorder module 226 can build a journal entry describing the traversal of a particular route in substantially real time (i.e., during traversal of the route). Data recorder module 226 also preferably supports an interface through which a route recorded by data recorder module 226 can be exported to route database 52 for subsequent viewing, selection and scheduling within a user's training journal.

The exemplary software configuration of server computer system 42 finally includes visualization module 230. Visualization module 230 supports one or more interfaces through which users of remote client computer systems 44 can view and/or annotate the data recorded within training journal database 54 by data recorder module 226. In the depicted embodiment, visualization module 230 includes training journal interface 232, which, as described in detail below, permits an athlete 14 to view and/or annotate a journal entry describing a route traversed during a fitness activity after completion of the route traversal. In a preferred embodiment, visualization module 230 further includes a real-time interface 234 through which a user at a remote client computer system 44 may view, in substantially real time, data logged within training journal database 54 for one or more athletes. Thus, for example, a spectator having access to Internet 40 can view the real-time standings of multiple competitors in a fitness activity, such as a marathon, cycling race, or other competitive event. Similarly, a remotely located trainer having access to Internet 40 via a client computer 44 can view the progress of one or more athletes 14 engaged in one or more training activities in substantially real time.

Visualization module 230 also preferably includes support for the export of selected journal entries between accounts of different users of the back-end service provided by server computer system 42. For example, visualization module 230 preferably permits a user to transmit a journal entry representing a traversal of a route via email. In addition, visualization module 230 may permit a user to create a "buddy" account that may be accessed and even annotated by guest users. In this manner, if the services provided by server computer system 42 are provided for a subscription fee, marketing of the service is enhanced by the ability of non-subscribers or subscriber having reduced-cost subscriptions to view journal entries created by exercise partners.

Referring now to FIGS. 4A-4F, there are illustrated a sequence of graphical user interface (GUI) windows presented by route wizard 222 to a user of client computer system 44 by HTTP server 214. As noted above, route wizard 222 provides a graphical and intuitive interface through which a remote user can automatically build, search for, and/or schedule routes to be traversed during a fitness activity.

In order to access route wizard 222, a user stationed at a remote client computer system 44 first logs into server computer system 42 via Internet 40 and HTTP server 214. As is well known to those skilled in the art, the login process typically includes the entry by the remote user of a login ID and password or other authentication information to server computer system 42, which then authenticates the identity of the user by reference to the user database or the like.

Following the preliminary authentication process, an exemplary embodiment of route wizard 222 first presents a graphical user interface (GUI) window 250 to the user. Within GUI window 250, the user is prompted to select one of three options 252, 254 and 256, which are each associated with a respective one of radio buttons 258a-258c. Thus, the user is permitted to build a new route (option 252), search for an existing route within route database 52 (option 254), and access one or more routes within a pre-packaged training plan (option 256). After the user has indicated a preference among options 252-256 by selecting one of radio buttons 258a-c utilizing cursor 262 or a keyboard, the user selects Next button 260 to proceed to the next step.

If the user selected option 256 indicating that the user desires to select a pre-packaged training plan, route wizard 222 may subsequently present the user with one or more additional windows in which a training plan meeting the user's needs and desires is designed. Route wizard 222 then automatically populates the training journal of the user with a schedule of fitness activities that conform to the distance, time and/or other parameters of the training plan. Thereafter, the user may be permitted to build or search for routes within route database 52 as described below with respect to FIGS. 4B-4F in order to fulfill the requirements of the scheduled fitness activities.

Figure 4A:
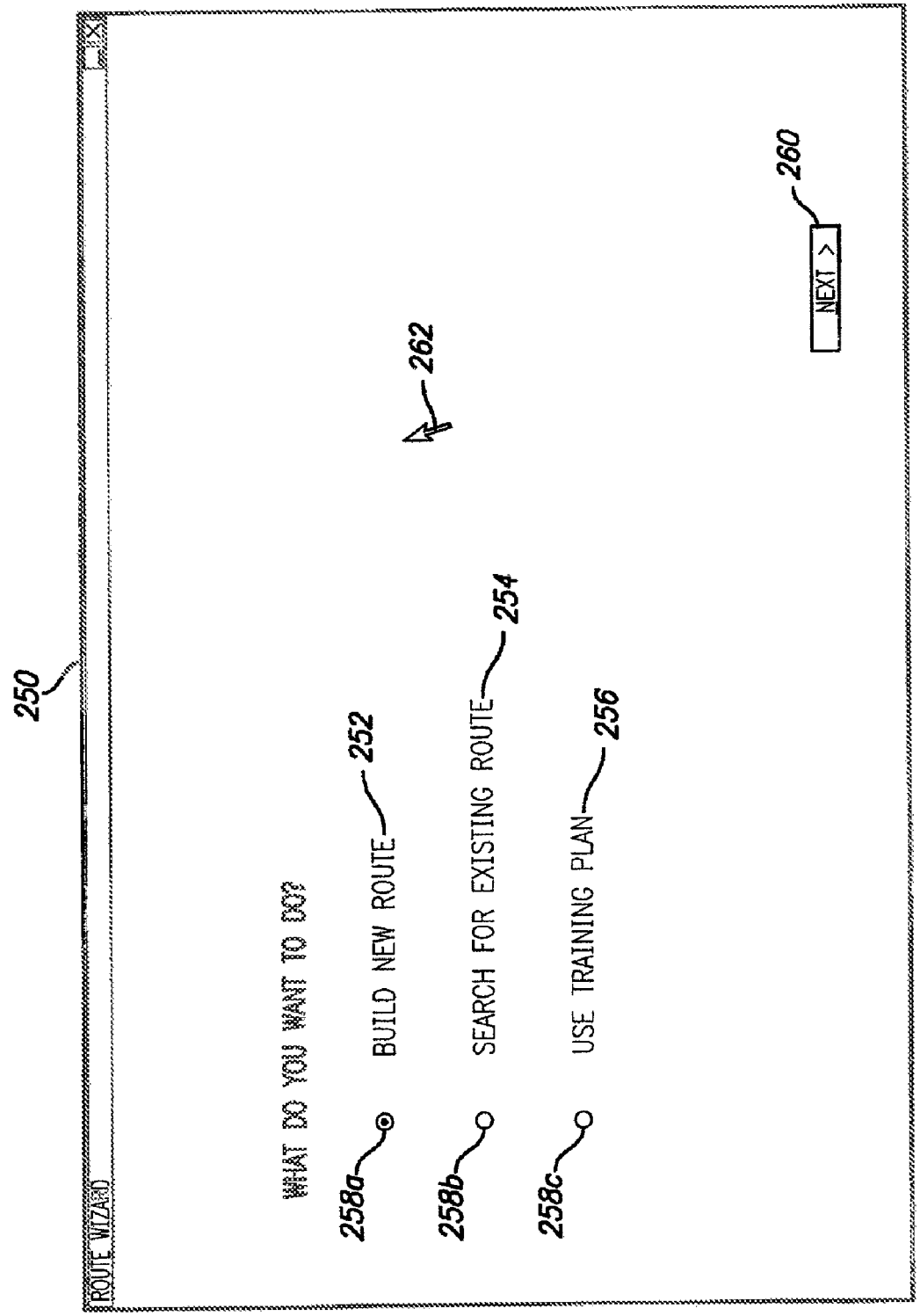
FIG. 4A depicts an exemplary graphical user interface of a route wizard through which a remote user may build a route, search for a route within a route database, and select routes within a predetermined training plan.
Figure 4B:
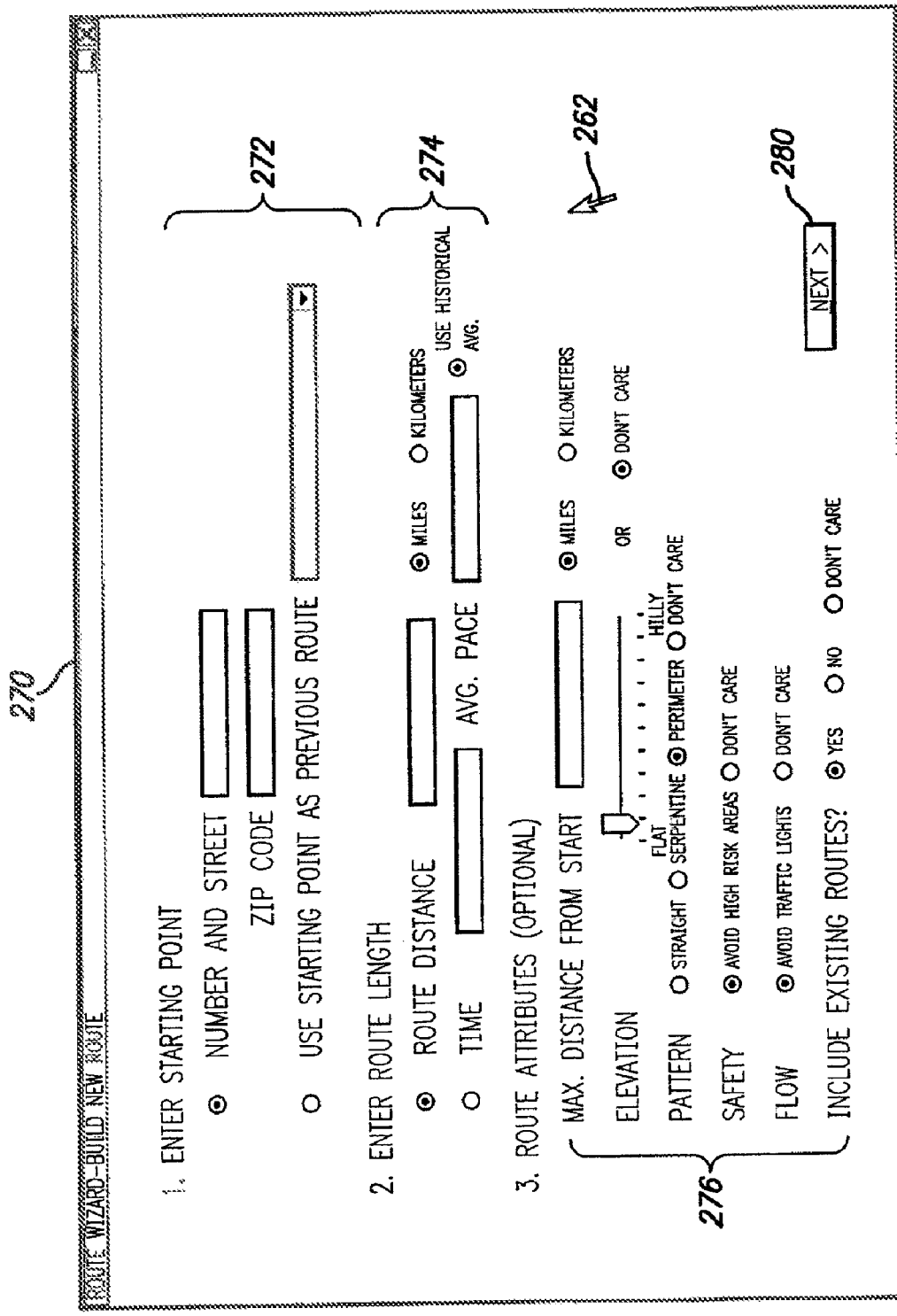
FIG. 4B illustrates an exemplary route wizard graphical user interface through which a user may enter parameters and attributes of a new route.

Assuming that the user selects option 252 of GUI window 250 in order to build a new route, route wizard 222 next presents to the user the GUI window 270 shown in FIG. 4B. As shown in FIG. 4B, window 270 includes a number of GUI components prompting the user to enter parameters for the new route to be built and, optionally, desired attributes of the route.

Specifically, the user is first prompted in section 272 to designate a starting point of the route (which in this embodiment is also the ending point) by entering a street address or ZIP code or by selecting a route within route database 52 having the desired starting point. Next, the user is prompted in section 274 to enter a desired overall length of the route, specified either by distance or by time. If time is utilized to specify the length of the route, a desired or historical average pace is preferably entered so that a route distance can be computed. In addition to the route parameters collected in sections 272 and 274, GUI window 270 may also prompt the user to enter optional route attributes. In the illustrated embodiment, the optional route attributes include a maximum distance that the route may extend from the starting point, a desired elevation profile of the route, a desired pattern of the route, a desired safety characterization of the route, a desired flow of the route, and whether or not the route may be a pre-existing route stored within route database 52.

Once the user has entered all required parameter and any optional route attributes within GUI window 270, the user selects Next button 280 utilizing cursor 262. In response, route generation and publication module 220 builds one or more routes conforming as closely as possible to the route parameters and route attributes entered through GUI window 270. The presentation of such routes by route wizard 222 is described below with respect to FIG. 4E.

Figure 4C:
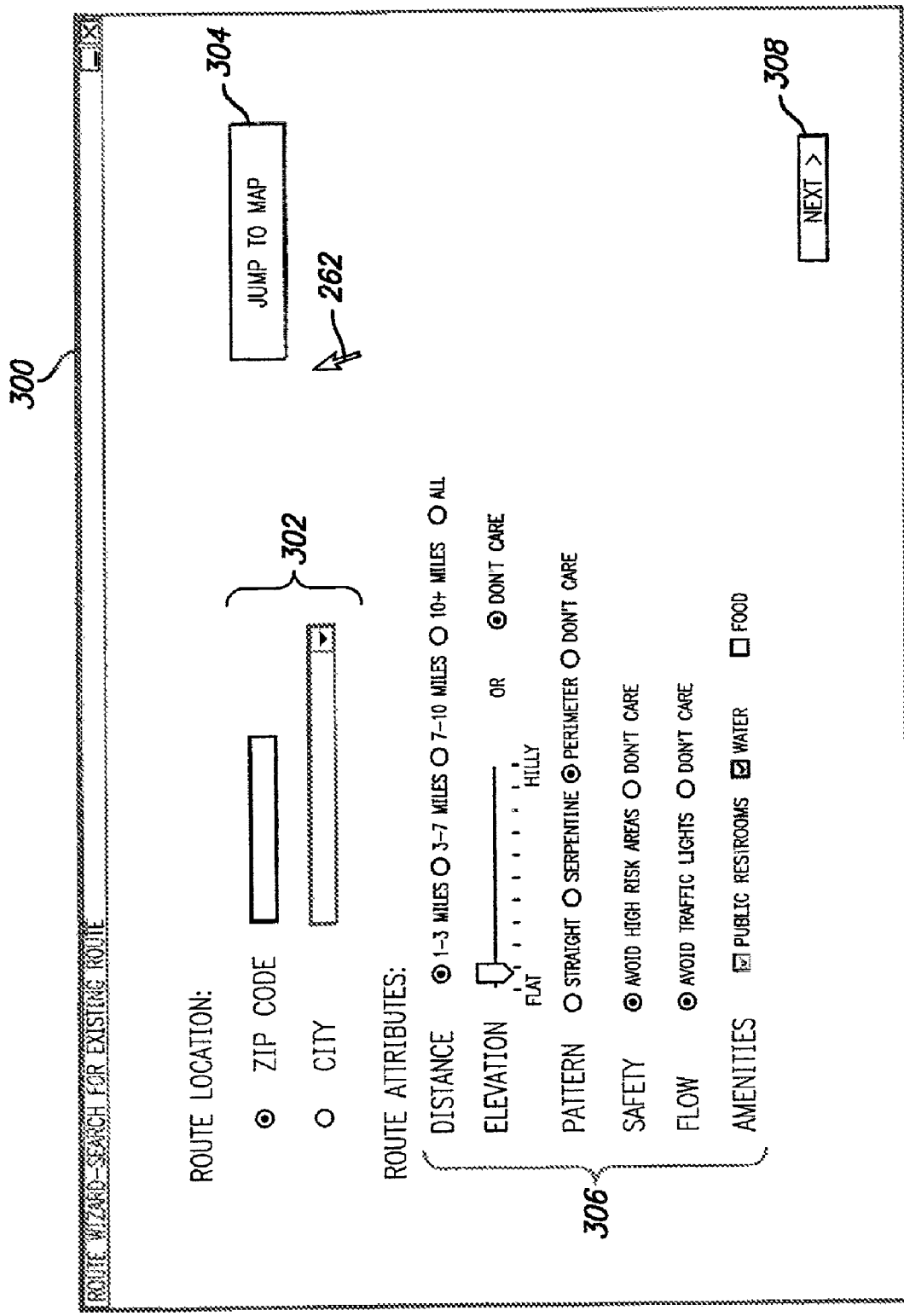
FIG. 4C depicts an exemplary route wizard graphical user interface through which a user may search a route database for an existing route.

Referring now to FIG. 4C, there is illustrated an exemplary embodiment of a GUI window 300 presented by route wizard 222 to a user of client computer system 44 is response to selection of option 254 in GUI window 250 of FIG. 4A. That is, in response to a user input indicating that the user desires to search for a pre-existing route within route database 52, route wizard 222 prompts the user through GUI window 300 to enter parameters and attributes of routes of interest to the user.

In the depicted embodiment, GUI window 300 includes two modalities by which the user may specify parameters for the route. In particular, in section 302, the user is permitted to specify a location of the route by ZIP code or city name. Alternatively, as represented by button 304, the user may specify a geographic location of the route or routes to be located by the search through a map interface. For example, if the user selects button 304 utilizing cursor 262, route wizard 222 may present window 320 of FIG. 4D, which is described below.

Still referring to FIG. 4C, in section 306 of GUI window 300, the user is permitted to input into route wizard 222 desired attributes of the route to be located through the search of route database 52. For example, in the illustrated embodiment, the route attributes include a range of route distance, an elevation profile, a route pattern, a route safety profile, a route flow, and amenities adjacent to the route. After the user has successfully entered a route location and any desired route attributes, the user may select Next button 308 utilizing cursor 262 to invoke a search of route database 52 by route generation and publication module 220 to locate one or more routes, if any, characterized by the desired route location and any route attributes. Assuming route generation and publication module 220 locates one or more routes of interest within route database 52, route wizard 222 presents the routes to the user through an interface such as that depicted in FIG. 4E, which is described below.

Figure 4D:
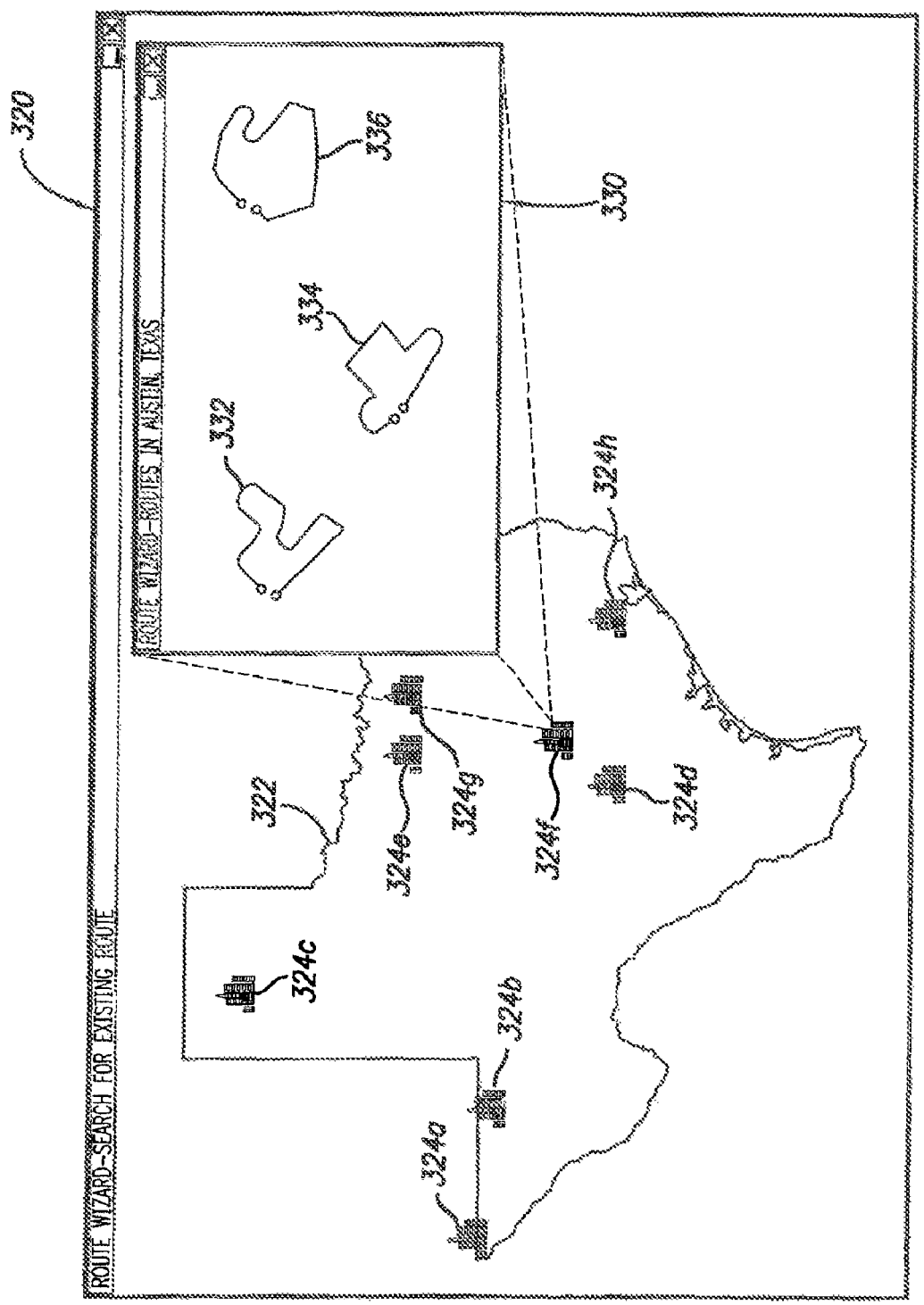
FIG. 4D illustrates an exemplary route wizard graphical user interface that presents a navigable geographical map populated with graphical indications of locations for which preexisting maps are stored within the route database.

Referring now to FIG. 4D, there is illustrated an exemplary GUI window 320 in which route wizard 222 presents a navigable geographical map populated with graphical indications of locations for which preexisting routes are stored within the route database 52. In the depicted embodiment, GUI window 320 includes a graphical representation 322 of a geographical area, for example, a political, cultural, or regional boundary. Within geographical representation 322, route wizard 22 presents a number of indicia 324*a-h* identifying geographic locations of one or more pre-existing routes for which route database 52 stores route data.

In response to the user flying over one of indicia 324 utilizing cursor 262, route wizard 222 displays in a separate window or frame 330 route maps 332-336 of the routes in the geographic location corresponding to the selected indicia 324. Graphical representations 332-336 may be advantageously presented overlaying a street or topographical map within window 330. If the user visually identifies one or more routes of interest at a particular geographical location through visual inspection of indicia 324 and/or the route maps 332-336 displayed within windows 330, the user may select that geographical location by clicking on the associated indicia 324. In this manner, GUI window 320 and its associated functionality provide the user with a graphical and intuitive way of viewing and selecting route locations of interest.

Figure 4E:
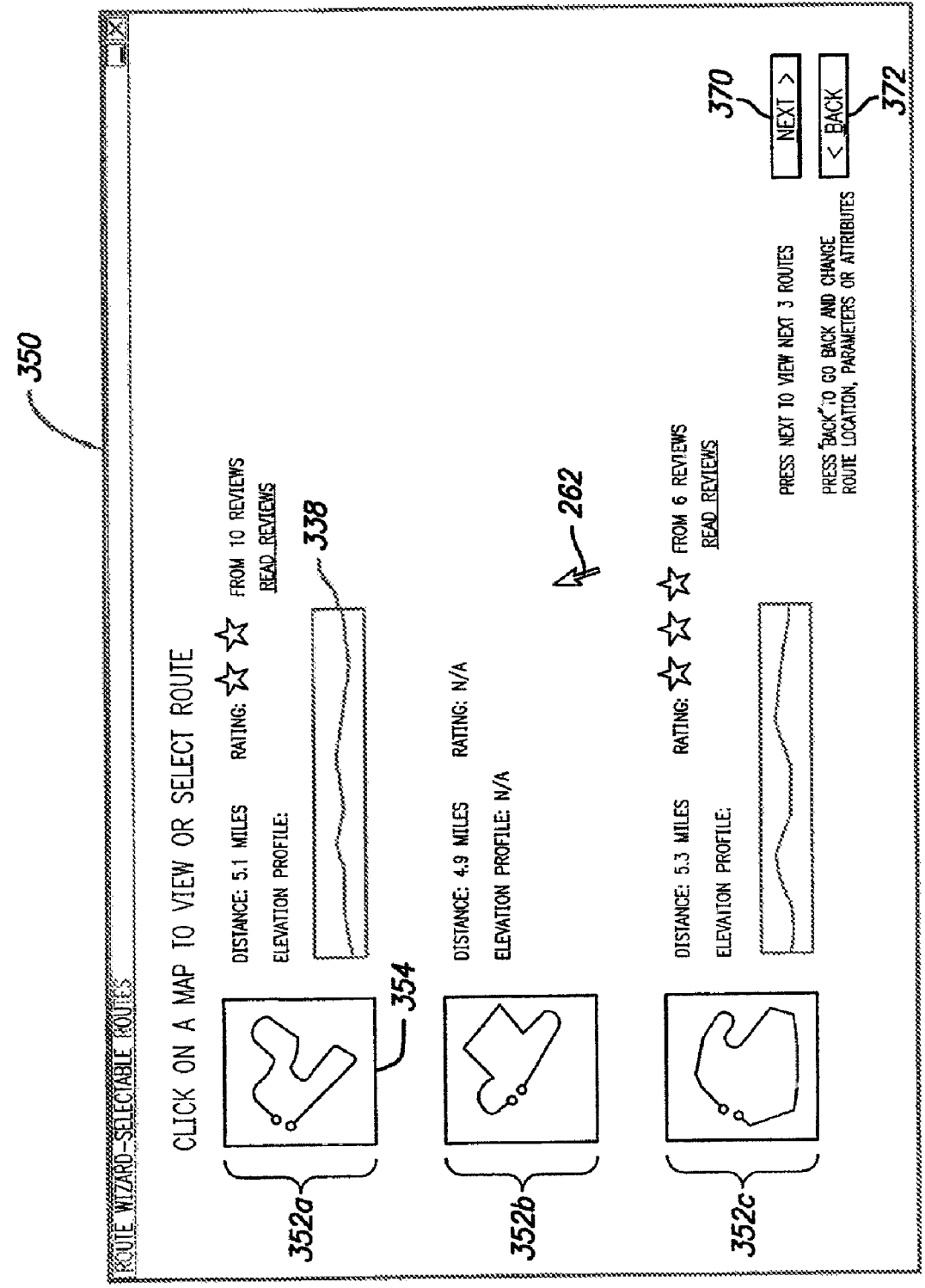
FIG. 4E depicts an exemplary route wizard graphical user interface within which a user may identify a selected route for detailed viewing.

With reference now to FIG. 4E, there is illustrated an exemplary GUI window 350 presented by route wizard 22 in order to permit a user to select from among one or more pre-existing routes that were located within route database 52 or that were built by route generation and publication module 220 in response to the input gathered by route wizard 222 within GUI window 270. As shown, in the depicted embodiment proposed routes that may be selected by the user are presented to the user in the form of route summaries 352*a-c*. Although such route summaries 352 may take any of a number of formats, in one preferred embodiment, each route summary 352 includes at least a route thumbnail 354 and a route distance 356. The route summary 352 may further include an elevation profile 358, which in the depicted embodiment is illustrated in graphical form, a route rating 360, and one or more audio or textual reviews or links thereto 362.

The user has a number of different navigation options from GUI window 350. First, by clicking on any of route thumbnails 354, the user is next presented with a graphical component through which the user may select or view detailed information regarding the selected route, as described further below with respect to FIG. 4F. Alternatively, the user may utilize cursor 262 to select Next button 370 in order to view one or more additional route summaries 352 of additional routes satisfying the user's route parameters and/or route attributes. In addition, by selecting Back button 372 utilizing cursor 262, the user is presented with one or more of the previously described GUI windows in order to permit the user to modify the route location or other route parameters or attributes.

Figure 4F:
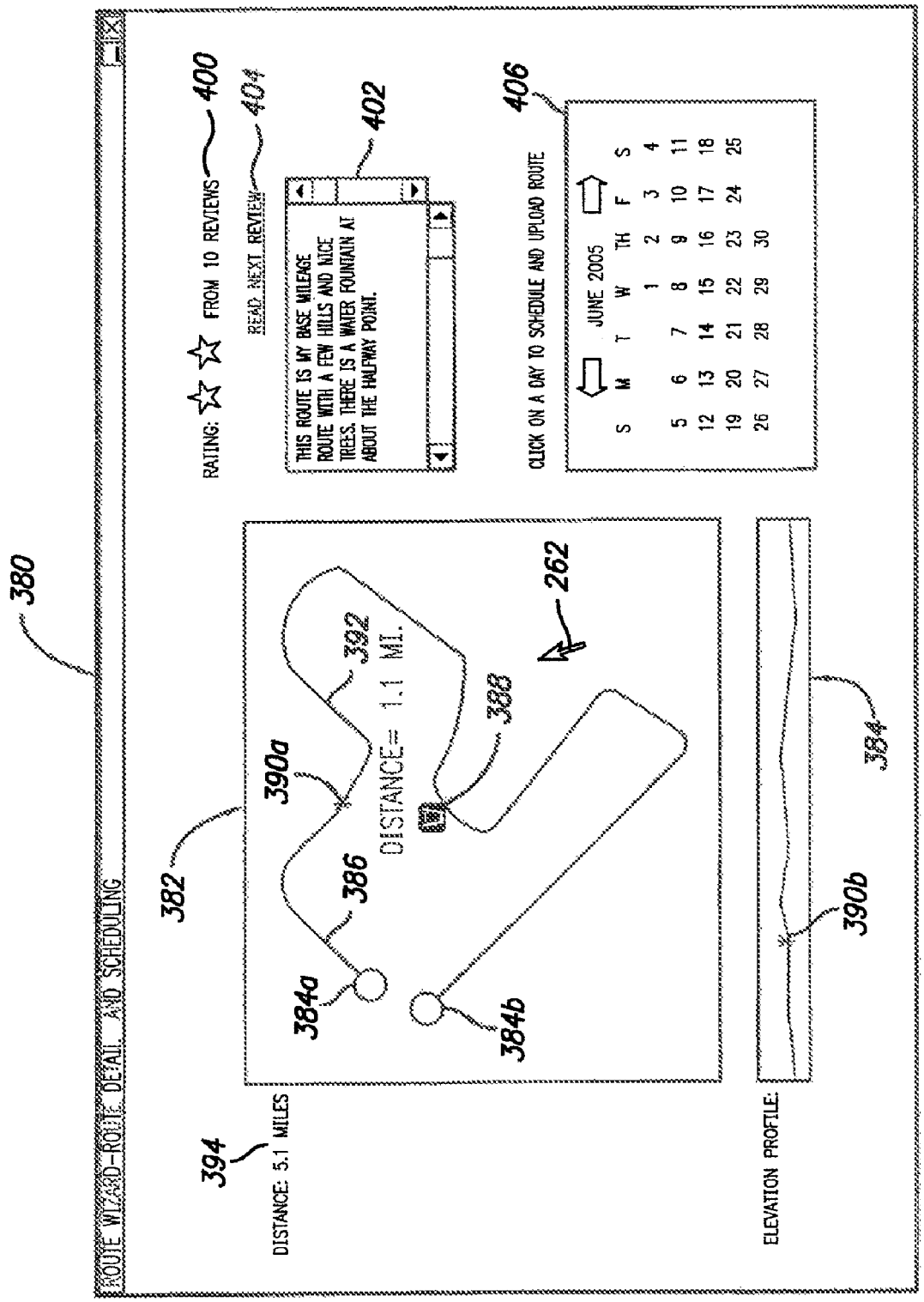
FIG. 4F depicts an exemplary route wizard graphical user interface that presents a detailed description of a route and permits the user to upload the route to a portable fitness device.

With reference now to FIG. 4F, there is illustrated an GUI window 380 presented by route wizard 222 to provide a detailed view of a proposed route and an interface through which the user can upload route data to portable training device 12 and schedule traversal of the route. In the illustrative embodiment, window 380 includes a detailed route map 382 indicating the geographical path of the route. Route map 382 includes terminal points 384*a*, 384*b* and a route path 386. Route map 382 may optionally further include one or more annotations 388 associated with a route, which may be stored in route database 52 or accessed from map database 224. For example, in FIG. 4F, route diagram 382 contains an annotation 388 indicating a geographical location of a potable water source.

By clicking on route path 386 utilizing cursor 262, the user invokes display by route wizard 222 of a marker 390*a*, which may then be selectively slid to any desired location along route path 386 utilizing cursor 262. Route wizard 222 preferably displays marker location information 392 in association with marker 390*a* to indicate the geographic location of marker 390 (e.g., the distance between marker 390*a* and terminal 384*a* along route path 386). In addition, route wizard 322 preferably displays a corresponding second marker 390*b* in association with elevation profile 384. In this manner, by manipulating either of markers 390*a* or 390*b* utilizing cursor 262, the user can visualize the location of particular elevation features or annotations 388.

As further shown in FIG. 4F, window 380 further includes a rating of the route, which in this case includes between one and four "stars" and an indication of a number of reviews. In addition, window 380 may optionally include a number of written reviews, for example, displayed within text box 402. The user may navigate to a next review of the route by selecting link 404.

GUI window 380 of FIG. 4F finally includes an interface through which the user may invoke the upload of route information pertaining to the route currently being viewed to portable training device 12. In the depicted embodiment, the user can invoke upload of the route information to portable training device 12 by scheduling the route utilizing calendar interface 406. For example, in order to upload route information pertaining to the illustrated route to portable training device 12, the user may select a desired date such as Jan. 16, 2004, by clicking on that date within calendar interface 406 utilizing cursor 262. In response to this input, route generation and publication module 220 enters the route to the athlete's training journal in training journal database 54 as a prospective event and uploads route information to portable training device 12 via Internet 40 and the wireless WAN. Importantly, in order to conserve data storage capacity within portable training device 12, the upload by route generation and publication module 220 is preferably deferred until a selectable time interval of the scheduled date. In this manner, route information is provided to portable training device 12 automatically and as needed.

Referring now to FIGS. 5A-C, there are illustrated a series of GUI windows presented by training journal interface 232 of visualization module 230 of server computer system 42 to permit a user to view, annotate and share training journal entries created utilizing data received over-the-air from portable fitness device 12. In order to access training journal interface 232, a user stationed at a remote client computer system 44 first logs into server computer system 42 via Internet 40 and HTTP server 214. As is well known to those skilled in the art, the login process typically includes the entry by the remote user of a login ID and password or other authentication information to server computer system 42, which then authenticates the identity of the user by reference to the user database or the like.

Following the preliminary authentication process, training journal interface 232 of visualization module 230 presents GUI window 420 to the remote user via HTTP server 214 and Internet 40. As illustrated, GUI window 420 includes a calendar interface 424 through which the user can select a past, current or future calendar month of interest utilizing cursor 262. An associated list box 422 presents for selection dates within the selected calendar month having journal entries within training journal database 54 for the specified login ID. Thus, by navigating utilizing cursor 262, the user can select for viewing journal entries detailing past or real-time routes previously traversed or currently being traversed by an athlete 14, or prospective routes scheduled for the athlete 14.

Assuming that the user selects a past journal entry within training journal database 54 from list box 422, training journal interface 232 presents GUI window 440 of FIG. 5B, again utilizing HTTP serve 214. As shown, the journal entry presented by training journal interface 232 within GUI window 440 provides detailed information regarding a route previously traversed by athlete 14, the athlete's performance, environmental conditions, as well as the athlete's personal comments and annotations.

In particular, the training journal entry presented within GUI window 440 includes a route map 442 having terminal points 444*a-b* and a route path 446 showing the geographical path traversed by the route. As discussed above, route map 442 may advantageously be presented as an overlay of a trail or street map retrieved from map database 224.

The overall performance of athlete 14, in traversing the route depicted in route map 442, is preferably summarized in a performance summary section 476. As indicated, performance summary section 476 may indicate the route distance, total elapsed time, average pace, average heart rate of athlete 14, as well as other route and performance information. Weather conditions at the time and geographical location at which athlete 14 traversed the route may optionally be presented in a weather condition section 478. For example, weather condition section 478 may specify the temperature, wind speed and direction, humidity, and precipitation. The weather condition information presented within weather condition section 478 may advantageously be accessed by visualization module 230 from any of the multiple publicly accessible weather databases available via Internet 40.

The user may interact with route map 442 in a number of ways. For example, the user may annotate route map 442 by dragging any of icons 460*a-f* to a selected location along route path 446 utilizing cursor 262. For example, in the illustrated embodiment, the user is dragging an annotation 454 representing a potable water source onto route map 442. The user may alternatively drag callout box icon 462 onto route map 442 in order to enter a textual annotation.

In addition, in response to clicking on route path 446 utilizing cursor 262, training journal interface 232 displays one or more markers 450*a*, 452*a* along route path 446, preferably in association with one or more items of route or performance information (e.g., a distance) for the geographical location identified by the marker 450*a*, 452*a*. By adding markers 450*a*, 452*a* in this manner, the user can graphically and intuitively ascertain the geographical location of features of interest and performance and route information at selected locations along route path 446. Training journal interface 232 may alternatively or additionally present route and performance information for a selected geographical location in response to the user causing cursor 262 to "fly over" the corresponding location on route path 446.

In association with route map 442, training journal interface 232 preferably presents other performance information, route information, and/or environmental information in graphical format. For example, in the depicted embodiment, training journal interface 232 presents an elevation profile 472*a*, a heart rate profile 472*b*, and a pace profile 472*c* in association with route map 442. When the user adds markers 450*a*, 452*a* to route path 446, training journal interface 232 automatically presents corresponding markers 450*b-d* and 452*b-d* at corresponding locations along graphical profiles 472*a-c*. As discussed above, all of markers 450 and all of markers 452 are synchronized so that movement of any of markers 450 moves all of markers 450 movement of any of markers 452 moves all of markers 452. In this manner, the user is able to graphically and intuitively define an interval over which performance, route and/or environmental information may be viewed. For example, in the depicted embodiment, interval information is depicted in interval section 474, which informs the user of the interval distance, time taken by the athlete to traverse the route interval, average pace over the route interval and average heart rate over the route interval.

Of course, the particular types of route, performance and environmental information shown in FIG. 5B are not exhaustive and other types of route, performance, and environmental information may be captured in association with the traversal of a route. If additional route, performance or environmental information is captured in association with the route, that information is preferably presented in a profile 472, within interval section 474, and/or within overall performance section 476 in like manner. For example, GUI window 440 may present information regarding what pair of shoes 24 the athlete was wearing during the fitness activity, together with a lifetime mileage total for that specific pair of shoes 24.

In a preferred embodiment of the present invention, the user may alternatively or additionally view route, performance and environmental information regarding a previously traversed route in an overlay view in which a graphical representation of the route, performance and/or environmental information is depicted along route path 446. For example, in the illustrated embodiment, in response to user selection of overlay view button 480 utilizing cursor 262, training journal interface 232 presents route map 500 of FIG. 5C in place of route map 442 of FIG. 5B.

Like route map 442, route map 500 includes terminal points 502*a* and 502*b* defining the starting and ending points of a route path 504. In contrast to route map 442, however, route path 504 of route map 500 comprises a plurality of bands 504*a-c*, each of which represents a respective route, performance or environmental parameter quantified at the waypoints recorded along the route. The value of the respective route, performance or environmental parameter is preferably charted along route path 504 utilizing gray scale or color shade variation to represent the instantaneous quantity of the route, performance or environmental parameter at each point along the route. Thus, in FIG. 5C, the different hatching applied to each of bands 504a-504c represents a different color and a varying spacing between the hatches represents the display of the colors at varying levels of intensity along the route path, depending upon the value of the parameters at each point along the path. The value associated with each shade of color or each level of gray scale is generally graphically represented in an accompanying legend 506. Training journal interface 232 preferably further presents instantaneous route and performance data at any point along the route path in response to a flyover of cursor 262 or in response to the user adding markers 508, 510 to the route path, as described above. For example, in association with the display of marker 508, training journal interface 232 displays information regarding the traversed distance, relative elevation, heart rate and pace associated with a distance 1.4 miles from the beginning of the route.

Returning to FIG. 5B, in addition to supporting user annotation of route maps 442 and 500, GUI window 440 preferably permits the user to enter additional information regarding environmental and route conditions and personal thoughts. For example, GUI window 440 includes a route condition section 482 that permits the user to record the surface and traffic conditions observed along the route, as well as a text box 484 in which the user may enter personal reflections about the training activity.

Finally, GUI window 440 preferably includes a GUI component that permits the user to review and/or rate the route. For example, in the exemplary embodiment, GUI window 440 contains a second text box 492 in which the user can compose a review of the route and a ratings section 494 in which the user can award the route between one and four "stars". After the route has been reviewed and/or rated, the user can select Publish button 496, which causes training journal interface 232 to store the review and rating within route database 52 in association with the route. In this manner, the review and rating are available for access by other users through route wizard 222, as described above.

Training journal interface 232 preferably permits a user to view prospective routes that have been scheduled utilizing a similar interface to that illustrated in FIG. 5B. In particular, in response to a user selecting a journal entry for a future date within list box 422 of FIG. 5A, training journal interface 232 presents a journal entry containing a route map 442 of the prospective training activity as shown in FIG. 5B. Of course, the journal entry will not contain any performance information (e.g., time, pace, heart rate, etc.) because the athlete 14 has not yet traversed the route.

Training journal interface 232 also preferably permits a user to view routes currently being traversed in substantially real time through an interface similar to that depicted in FIG. 5B. In this case, training journal interface 232 presents a journal entry containing a route map 442 and a marker 450a showing the athlete's current location with respect to route path 446. In addition, training journal interface 232 may present a summary section 476 summarizing the athlete's performance to the current position, a weather condition section 478, an interval section 474, and one or more graphical profiles 472. In this manner, a remote trainer or spectator stationed at a client computer system 44 may track an athlete's performance information, route information and environmental information in substantially real time.

If a user stationed at a client computer system 44 desires to view a substantially real time view of the activities of multiple athletes traversing a common route, the user preferably logs into real-time interface 234 through HTTP server 214. Assuming the user has the appropriate subscription and/or permissions, real-time interface 234 builds from the training journals of multiple athletes a web page containing a single route map on which multiple markers, each representing a respective athlete, are presented. The web page may further present separate performance and route information for each athlete. In this manner, a remote trainer or spectator stationed at a client computer system 44 may track performance information, route information and environmental information in substantially real time for multiple athletes traversing the same or substantially the same route.

While the invention has been particularly shown as described with reference to a preferred embodiment, it will be understood by those skilled in the art that various changes in form and detail may be made therein without departing from the spirit and scope of the invention. For example, it will be appreciated that the concepts disclosed herein may be extended or modified to apply to other types of configuration entities having different rules than the particular exemplary embodiments disclosed herein. In addition, although aspects of the present invention have been described with respect to a computer system executing software that directs the functions of the present invention, it should be understood that present invention may alternatively be implemented as a program product for use with a data processing system. Programs defining the functions of the present invention can be delivered to a data processing system via a variety of signal-bearing media, which include, without limitation, non-rewritable storage media (e.g., CD-ROM), rewritable storage media (e.g., a floppy diskette or hard disk drive), and communication media, such as digital and analog networks. It should be understood, therefore, that such signal-bearing media, when carrying or encoding computer readable instructions that direct the functions of the present invention, represent alternative embodiments of the present invention.

In addition, while the present invention has been described with respect to an exemplary software configuration in which software performing certain functions of the present invention resides on a server computer system of a service provider (e.g., of a subscription service), those skilled in the art will appreciate that, in alternative embodiments, such software may alternatively reside on a client computer system, such as client computer system 44, and/or on portable fitness device 12.

Furthermore, while the present invention has been described with reference to tracking and visualizing the performance and/or route of an athlete, those skilled in the art will appreciate that the present invention may also be applied to tracking and visualizing the location and movement of other persons, such as children or criminals under electronic supervision, or objects.

What is claimed is:
1. A method for execution by a server computer system, the method comprising:
receiving a description of a fitness activity of interest to a user;
in response to receiving the description, identifying a route corresponding to the activity of interest; and
initiating the presentation of a route rating associated with the route that is based upon at least one individual rating associated with the route.

2. The method of claim 1, wherein the description includes a geographic location.

3. The method of claim 1, wherein the description includes an indication of difficulty.

4. The method of claim 1, wherein the description includes a time.

5. The method of claim 1, wherein the description includes a distance.

6. The method of claim 1, wherein the description includes an average pace.

7. The method of claim 1, wherein the description includes an elevation.

8. The method of claim 1, wherein the step of identifying the route includes building the route in response to receipt of the description.

9. The method of claim 1, wherein the step of identifying the route includes locating the route in a database containing a plurality of routes.

10. The method of claim 1 further comprising the step of initiating presentation of a graphical element corresponding to the route.

11. The method of claim 10 further comprising the step of initiating the presentation of a map with a marker located thereupon indicating a location with which one or more routes, including the route corresponding to the activity of interest, are associated,
wherein the step of initiating the presentation of the graphical element occurs in response to receiving a selection of the marker located on the map.

12. The method of claim 10, wherein the graphical element includes a visual depiction of the route.

13. The method of claim 10, wherein the step of initiating the presentation of the route rating occurs simultaneously with the step of initiating the presentation of the graphical element.

14. The method of claim 1, wherein the route rating is conveyed by displaying one or more icons.

15. The method of claim 14, wherein the one or more icons are stars.

16. The method of claim 1, wherein the route rating includes written feedback.

17. The method of claim 1, wherein the route rating is accompanied by an indication of the number of individual ratings that the route rating is based on.

18. The method of claim 1, wherein the at least one individual rating associated with the route was received via a wireless transmission from a mobile device.

19. The method of claim 1, wherein:
the user is a first user; and
the at least one individual rating was provided by a second user who is different from the first user.

20. The method of claim 1, wherein the server computer system is located remotely from a portable fitness device, and the presentation occurs at the portable fitness device.

21. The method of claim 1, wherein the description of the fitness activity of interest is a description of a prospective fitness activity of interest.

22. The method of claim 1, wherein the route is a prospective route to be physically traversed by the user.

23. The method of claim 1, wherein the route is comprised of a series of geographical waypoints.

24. The method of claim 1, further comprising:
initiating the downloading of information describing the route to a remotely located portable fitness device.

25. A computer program product comprising non-transitory computer-useable medium having computer program logic recorded thereon that, when executed by one or more processors of a server computer system, provides information about a route corresponding to a fitness activity of interest to a user, the computer program logic comprising:
first computer readable program code that enables a processor to receive a description of the fitness activity of interest to the user;
second computer readable program code that enables a processor to, in response to receiving the description, identify a route corresponding to the activity of interest; and
third computer readable program code that enables a processor to initiate the presentation of a route rating associated with the route that is based upon at least one individual rating associated with the route.

26. The computer program product of claim 25, further comprising fourth computer readable program code that enables a processor to initiate the presentation of an indication of the number of individual ratings that the route rating is based on.

27. The computer program product of claim 25, further comprising fourth computer readable program code that enables a processor to initiate the presentation of a graphical element corresponding to the route.

28. The computer program product of claim 27, wherein the third computer readable program code and the fourth computer readable program code enable the presentation of the route rating to occur simultaneously with the presentation of the graphical element.

29. The computer program product of claim 25, wherein:
the user is a first user; and
the at least one individual rating was provided by a second user who is different from the first user.

30. A method for execution by one or more processors, the method comprising:
receiving a description of a fitness activity of interest to a user;
in response to receiving the description, identifying a route corresponding to the activity of interest; and
displaying a characteristic associated with the route that is based upon at least one individual input associated with the route.

31. The method of claim 30, wherein the characteristic is a route rating and the individual input is an individual rating.

32. The method of claim 31, wherein the individual rating is an individual rating of the route.

33. The method of claim 32, wherein:
the user is a first user;
the individual rating was provided by a second user who is different from the first user; and
the individual rating is based on the second user's assessment of the quality of the route.

34. The method of claim 32, wherein:
the user is a first user;
the individual rating was provided by a second user who is different from the first user; and
the individual rating is based on the second user's athletic performance while traversing the route.

35. The method of claim 34, wherein the individual rating is determined based on feedback from one or more sensors supported by the second user during traversal of the route.

36. The method of claim 30, wherein:
the method further comprises scheduling a prospective traversal of the route in a training plan of the user on a server at a first time for traversal at a second time; and
transmitting data associated with the route from the server to a mobile device after the first time and before the second time.

37. The method of claim 36, wherein the step of scheduling the prospective traversal of the route in the training plan of the user includes associating the prospective traversal of the route with a particular date.

38. The method of claim 36, wherein the data associated with the route is route map data.

39. The method of claim 36, wherein the data associated with the route is a sequence of turn-by-turn instructions.

40. The method of claim 30, wherein the description of the fitness activity of interest is a description of a prospective fitness activity of interest.

41. The method of claim 30, wherein the route is a prospective route to be physically traversed by the user.

42. The method of claim 30, wherein the route is comprised of a series of geographical waypoints.

* * * * *